(12) United States Patent
Yin et al.

(10) Patent No.: US 7,476,369 B2
(45) Date of Patent: Jan. 13, 2009

(54) APPARATUS FOR STEAM STERILIZATION OF ARTICLES

(75) Inventors: Xiang-Dong Yin, Ontario (CA); Gabriel Neagoe, Ontario (CA); Dorin Cioraca, Ontario (CA); Andy Kwan-Leung Sun, Ontario (CA)

(73) Assignee: SciCan Ltd., Toronto (CA)

( * ) Notice: Subject to any disclaimer, the term of this patent is extended or adjusted under 35 U.S.C. 154(b) by 500 days.

(21) Appl. No.: 10/662,404

(22) Filed: Sep. 16, 2003

(65) Prior Publication Data

US 2005/0058571 A1   Mar. 17, 2005

(51) Int. Cl.
*A61L 2/04* (2006.01)
*A61L 2/08* (2006.01)
*F22B 27/00* (2006.01)

(52) U.S. Cl. .................... 422/298; 422/26; 392/399

(58) Field of Classification Search .................. 422/26, 422/307, 109; 392/324, 399; 122/40
See application file for complete search history.

(56) References Cited

U.S. PATENT DOCUMENTS

| | | | |
|---|---|---|---|
| 2,490,547 A * | 12/1949 | Schraner et al. ............. 392/399 |
| 2,622,184 A | 12/1952 | Johneas | |
| 3,750,399 A * | 8/1973 | Moore .......................... 60/670 |
| 4,881,493 A * | 11/1989 | Riba ........................... 392/400 |
| 5,271,893 A | 12/1993 | Newman | |
| 5,290,511 A | 3/1994 | Newman | |
| 5,350,901 A * | 9/1994 | Iguchi et al. ................ 219/630 |
| 5,805,765 A | 9/1998 | Altman | |
| 5,835,678 A * | 11/1998 | Li et al. ....................... 392/401 |
| 6,067,403 A * | 5/2000 | Morgandi ..................... 392/401 |
| 6,299,076 B1 | 10/2001 | Sloan et al. | |
| 6,379,613 B1 | 4/2002 | Stempf | |
| 6,521,047 B1 * | 2/2003 | Brutti et al. .................. 118/726 |
| 6,577,815 B1 | 6/2003 | Wu | |
| 2003/0035752 A1 | 2/2003 | Aksenov et al. | |
| 2004/0004299 A1 * | 1/2004 | Glucksman ................. 261/129 |

FOREIGN PATENT DOCUMENTS

| | | |
|---|---|---|
| DE | 35 12 370 A1 | 10/1986 |
| EP | 1 010 937 A1 | 6/2000 |
| WO | WO 97/33479 | 9/1997 |
| WO | WO 01/75360 A1 | 10/2001 |

* cited by examiner

*Primary Examiner*—Elizabeth L McKane
*Assistant Examiner*—Kevin C Joyner
(74) *Attorney, Agent, or Firm*—Clark & Brody

(57) ABSTRACT

A steam on demand generator uses a stainless steel cup and cap arrangement and hollow cone spray nozzle. The nozzle directs a cone of water onto a wall of the cup. A heating device and a thermocouple are brazed to the cup, with the thermocouple positioned on a part of the wall to enhance control of the operation and steam generation.

6 Claims, 3 Drawing Sheets

APPARATUS FOR STEAM STERILIZATION OF ARTICLES

FIELD OF THE INVENTION

The present invention is directed to a method and apparatus for the steam sterilization of articles, and in particular to a method and apparatus employing a stainless steel steam generator with a brazed thermocouple and spray nozzle combination for improved steam-on-demand generation.

BACKGROUND ART

In the prior art, the use of steam generators to sterilize articles for medical procedures and the like is well known. One type of steam generator for sterilization of articles is disclosed in U.S. Pat. Nos. 5,271,893 and 5,290,511 to Newman, herein incorporated in their entirety by reference herein. In these patents, a boiler operates as a flash boiler wherein water supplied to the boiler is immediately evaporated so that the boiler stays essentially dry during steam generation. The temperature of the boiler is monitored using a temperature sensor placed inside the boiler, whereby evaporation of the water is signified by a sharp increase in the boiler temperature. Water is injected into the boiler at this time to generate additional steam, and the process is repeated continually to supply steam while keeping the boiler in a dry state. The water is injected using a dosing pump and a conduit having an end positioned near the bottom of the chamber of the boiler. The thus-generated steam exits the boiler in another conduit and enters a sterilizing cassette.

While these steam-on-demand boilers offer significant advantages over other types of steam generators, the boilers are made of aluminum, which is cast around its heating coils. The aluminum material tends to oxidize over time. The oxides can coat the temperature sensor and affect its performance. Moreover, steam generation output is sensitive to the manner in which the water is injected into the boiler chamber and placement of the temperature sensor, and steam output can sometimes suffer due to improper water injection and sensor placement.

Therefore, a need exists to improve the generation of steam using steam-on-demand generators. In response to this need, the present invention provides an improved steam-on-demand generator that has improved corrosion resistance, and better steam generation capability.

SUMMARY OF THE INVENTION

It is a first object of the present invention to provide an improved steam-on-demand generator.

Another object of the invention is a steam-on-demand generator having a stainless steel chamber and brazed construction.

One other object of the invention is a method of generating steam on demand using the inventive steam generator.

Other objects and advantages of the present invention will become apparent as a description thereof proceeds.

The invention is an improvement in the steam-on-demand generators of the prior art, particularly those disclosed in the aforementioned Newman patents. In one aspect, the invention relates to a steam on demand generator that has a cup assembly, a heating device for heating the cup assembly and an interior thereof, a water injection device for supplying water to the cup assembly, a steam outlet, and a temperature sensor positioned within the cup assembly. Water is supplied in quantities so that the interior of the cup assembly remains essentially dry during steam generation. The invention is an improvement over these types of steam generators in that the cup assembly includes a thin-walled stainless steel cup and stainless steel cap forming the interior. A hollow cone spray nozzle in the stainless steel cap is provided for supplying water to the cup. The heating device and a temperature sensitive portion of the temperature sensor are brazed to the stainless steel cup.

An end portion of the temperature sensor is preferably brazed at a location on an inside wall of the stainless steel cup, the inside wall receiving spray from the hollow cone spray nozzle. The temperature sensor can be a thermocouple and at least a side of a tip of the thermocouple should directly contact the inside wall via the brazing, with an end surface or face of the sensor remaining exposed after brazing.

The cup of the steam generator is configured with a wall portion that both receives the spray from the nozzle and serves as an attachment point for the temperature sensor.

The heating device can be a heating coil that surrounds a lower portion of the cup assembly, with the lower portion including the wall of the cup. The cup can also include a stainless steel stud that is brazed to a bottom of the cup, the stud providing a channel for the temperature sensor to enter the interior. The temperature sensor can be brazed to portion of the stud.

Another aspect of the invention is an improvement in the method of steam-on-demand generation. In the prior art method, water is dispensed into a cup of the steam generator in pulses to generate steam on demand while maintaining the steam generator essentially dry during steam generation. The injection of water is controlled by sensing a temperature of an interior of the steam generator and the cup. The invention improves upon this method by dispensing the water in a hollow cone spray pattern with the cone of atomized water contacting a wall of the stainless steel cup, and sensing the interior temperature and temperature of the cup using a temperature sensor placed on a portion of the upstanding wall receiving the dispensed water.

The temperature sensor can be a thermocouple and an end portion of the temperature sensor can be brazed to the wall with an end face of the end portion exposed after brazing. Control over steam generation can utilize a change of temperature sensed by the temperature sensor over time rather than just monitoring the change of temperature as has been done in prior art steam-on-demand generators.

Another aspect of the invention entails the cup and cap assembly for a steam generator. This assembly includes a cap having an opening for water dispensing, a cup, a clamp assembly securing the cap to the cup to form a sealed interior, a heating element brazed to the cup; and a temperature sensor. An end portion of the temperature sensor is positioned in the interior and brazed to a portion of a wall of the cup. At least the cap, the cup, the spray nozzle, and clamp assembly are stainless steel.

DESCRIPTION OF THE PREFERRED EMBODIMENTS

The present invention offers significant improvements in the generation of steam on demand for various applications, including sterilization of articles. While the inventive steam generator is preferably used to provide steam on demand for sterilization purposes, it can be used in other applications where steam is required.

The inventive generator overcomes many of the problems in prior art steam generators related to the presence of aluminum oxides that adversely affect temperature control. Use of a stainless steel construction for the steam generator components eliminates the problem with aluminum oxides. It also allows the use of thin walls for the steam generator, thus improving manufacturing costs, and enhancing heat conduction from the heating coils disposed on the outside of the thin walls.

The invention also solves the problem of attaching thermocouples or other temperature sensors to stainless steel materials through the use of brazing as the attachment mode. The inventive steam generator offers superior steam generation as well due to the use of a hollow cone spray nozzle, which directs the injected water in a cone pattern that strikes the hottest part of the boiler. Placement of the temperature sensor in this zone allows for precise control of steam generation.

Figure 1:
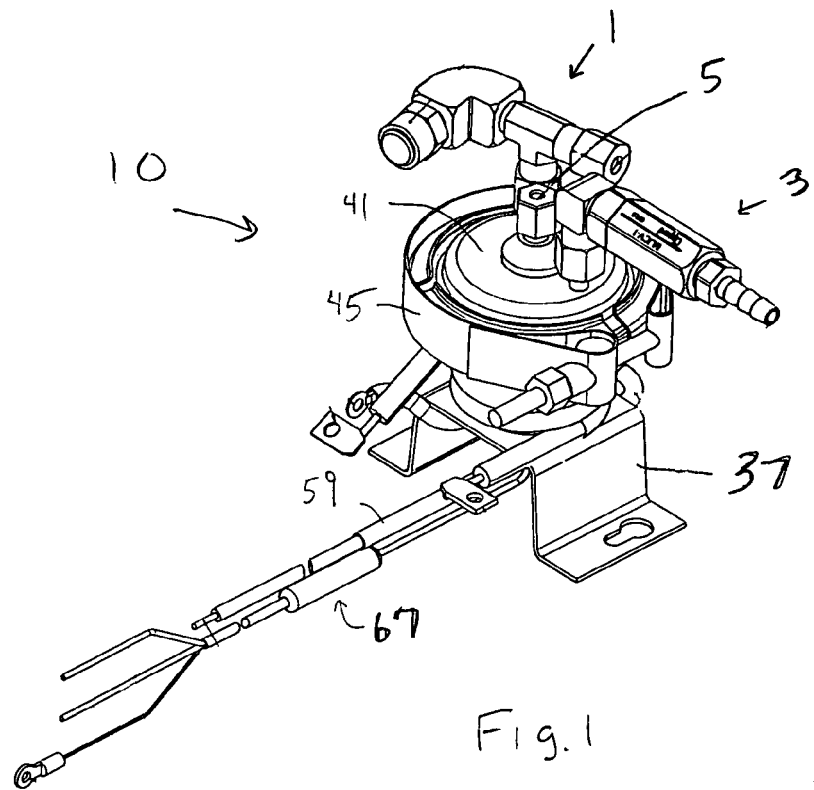
FIG. 1 is a perspective view of one embodiment of the inventive steam on demand generator.

Referring now to FIG. 1, the one embodiment of the inventive steam generator is generally designated by the reference numeral 10. The steam generator 10 includes a steam outlet assembly 1, an air inlet assembly 3, and a water inlet assembly 5.

Figure 2:
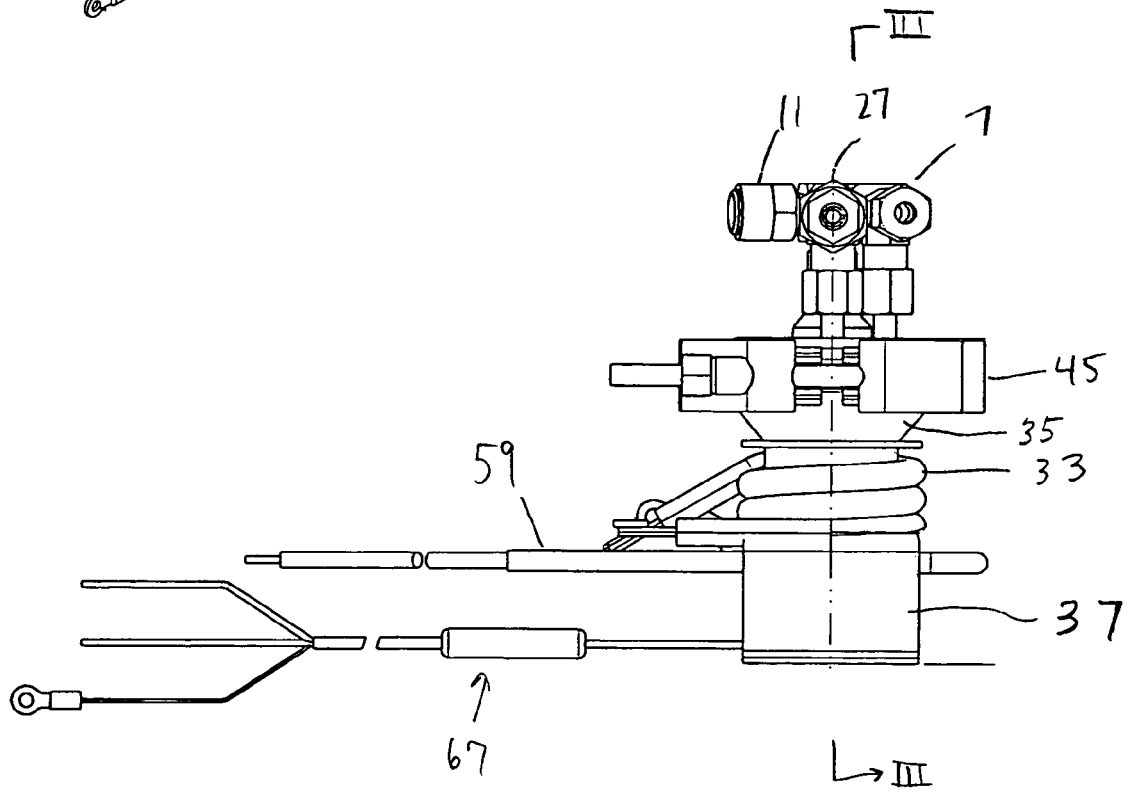
FIG. 2 is a side view of the steam on demand generator of FIG. 1.
Figure 3:
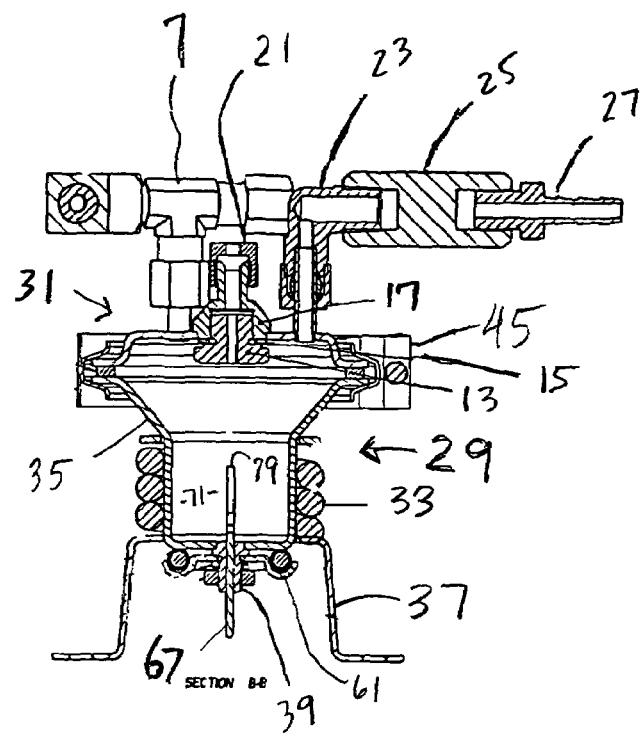
FIG. 3 is a cross sectional view along the line III-III of FIG. 2.
Figure 4:
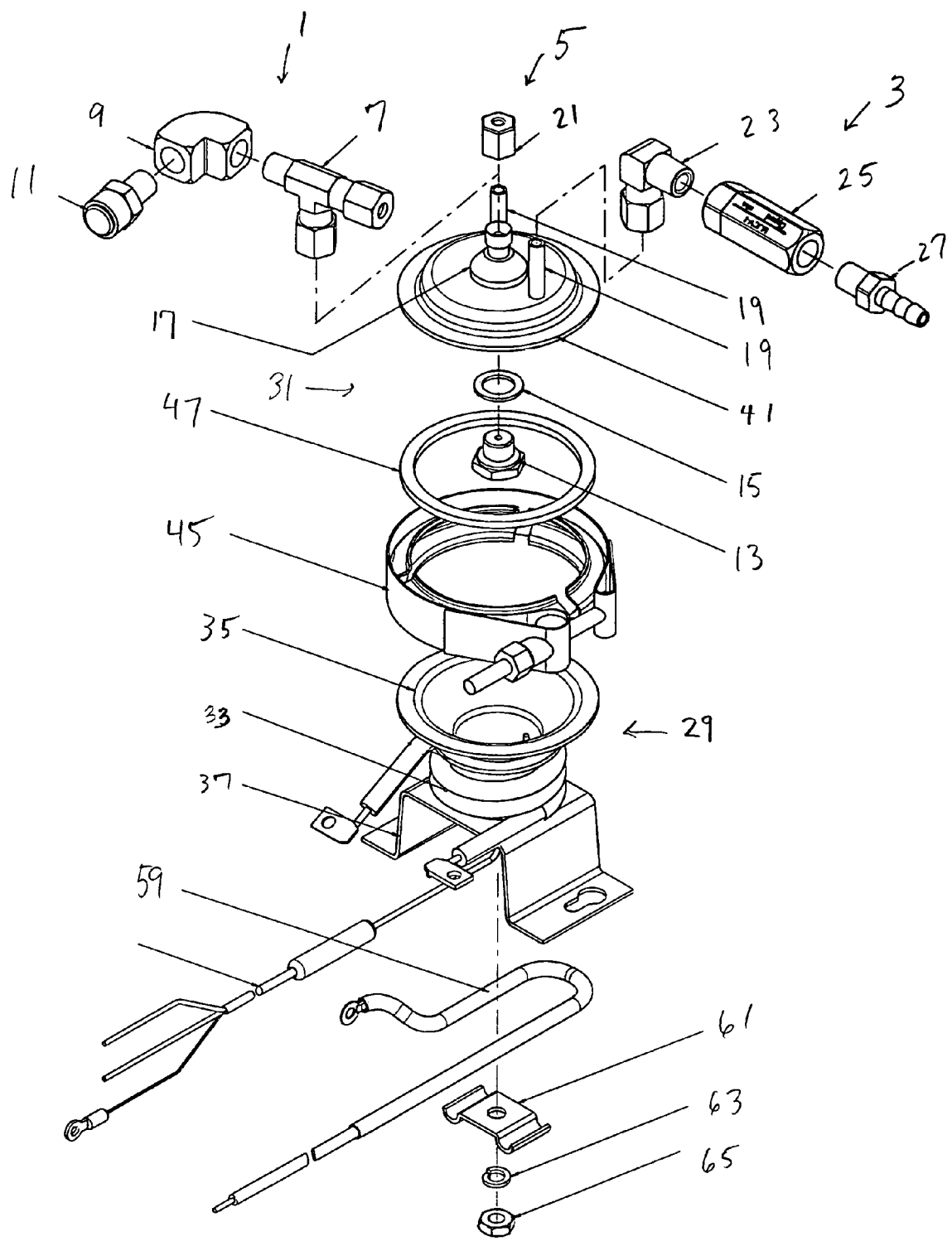
FIG. 4 is an exploded view of the steam on demand generator of FIG. 1.

Referring to FIGS. 2-4, and particularly to FIG. 4, the steam outlet assembly 1 includes tee fitting 7, elbow 9, and pressure relief valve 11. The water inlet assembly 5 includes spray nozzle 13, seal 15, nozzle adapter 17, and compression nut 21. The air inlet assembly 3 includes elbow compression fitting 23, check valve 25, and hose barb fitting 27. While it is preferred to have these components for outlet of steam, inlet of air, and inlet of water, other arrangements as would be within the skill of the art could be employed for these purposes. The steam outlet assembly 1 provides an outlet for steam to exit the generator 10 and be directed via a conduit (not shown) to a sterilizing cassette or other steam-requiring device. The air inlet assembly 3 allows air to enter the generator 10 for drying purposes once the steam is no longer in demand, and for other reasons as would be mandated by the particular use of the steam generator. Air supplied by a source (not shown) enters the hose barb 27, through check valve 25, and elbow 23, passes into the generator and exits via the steam outlet assembly 1.

Still referring to FIGS. 2-4, the generator 10 has a base half assembly 29 and a cap half assembly 31. The base half assembly 29 is made up of heating element 33, cup 35, bracket 37, and mounting stud 39 (see FIG. 3). The base half elements are attached together to form a unitary assembly, and are preferably attached together by brazing. Preferably, the brazing material is a copper based alloy but other materials can be used. The components of the base half assembly 29 are made of stainless steel, with the cup having a generally thin wall construction, e.g., wall thickness less than 1.52 mm, to minimize the heating load on the heating element. The heating element 33 is shown as a heating coil, but virtually any type of heating device compatible with the base half assembly 29 can be brazed or otherwise made part of the steam generator.

The cap half assembly 31 is made up of the cap 41, the nozzle adapter 17, and tubes 19. The tubes 19 connect to the elbow 23 and tee fitting 7, respectively, to allow egress of steam and ingress of air, respectively, to a chamber formed by the base and cap half assemblies 29 and 31. The components of the cap half assembly 31 are also preferably brazed together to form a unitary structure, with a preferred brazing alloy being a nickel-based alloy. Of course, other brazing alloys can be used in this application.

The base half assembly 29 and cap half assembly 31 are clamped together using a v-band stainless steel coupling 45 and silicone gasket 47. The gasket 47 assures a leak free seal between the cap 41 and cup 35 that form the steam generating chamber.

The steam generator 10 has two safety features, the pressure relief valve 11 noted above, and a thermal fuse 59. The fuse 59 is held in place using clamp 61, spring washer 63 and nut 65.

Figure 5:
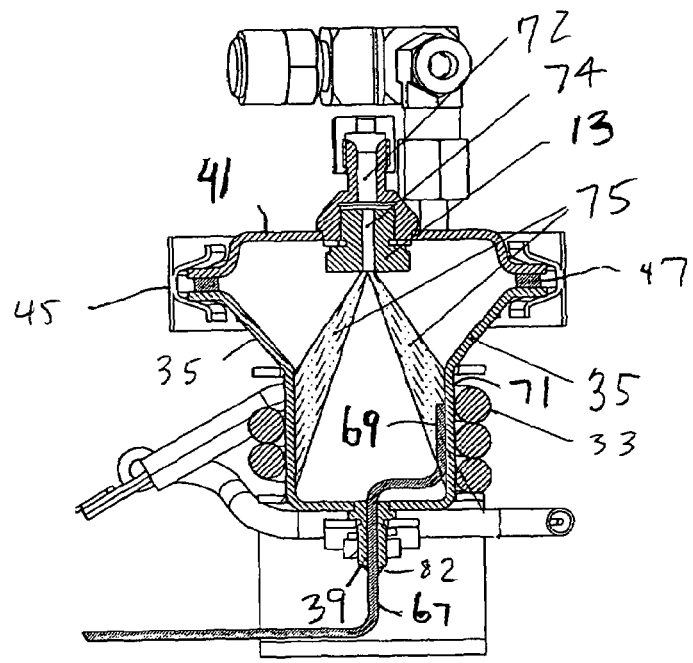
FIG. 5 is a sectional view of the steam on demand generator of FIG. 1 in operation.

The steam generator 10 also includes a thermocouple 67, but any temperature sensor could be used that would provide the proper control over the generation of steam. Referring to FIGS. 3 and 5, the thermocouple 67 extends through the mounting stud 39, along a bottom of the cup 35, and along an upstanding wall 71 of the cup 35, with an end portion 69 terminating at tip surface 79.

The thermocouple end portion 69 is brazed to the wall 71 under conditions, which are designed to maximize performance of the steam generator 10. More specifically, it is preferred to have the end portion 69 in a location that optimizes steam generation. If the thermocouple is improperly situated, then steam generation is compromised.

The thermocouple 67 is brazed in place on the wall 71 at the most thermally sensitive region. It is also preferred to form a brazed joint where the thermocouple meets an end portion 82 of the stud 39, see FIG. 5. The thermally sensitive region is where: (a) the thermocouple end portion 69 will experience the most rapid increase in temperature in the absence of water, and (b) experience the earliest decrease in temperature in the presence of water. In order to achieve item (a), the end portion 69 should be mounted at the hottest spot on the cup 35. Item (b) suggests that the thermocouple be mounted at the location where the largest amount of atomized water will hit during water spraying. In achieving these results, it is preferred to control the amount of brazing alloy used to attach the end 69 to the wall 71. Too much brazing alloy will adversely affect the control of the operation using the thermocouple. To little alloy will not provide the attachment to the wall to sense the wall temperature.

When brazing the thermocouple, it is preferred to have the thermocouple end portion 69, including the very tip portion of the end 69 in contact with the wall 71 of the cup 35. The top surface or end face 79, see FIG. 3, should be exposed and not covered by brazing material. The brazed fillet should be no more than half of the diameter of the thermocouple in size. A preferred length of the fillet along the wall 71 is about half of the wall height, the fillet beginning at the face 79 and extending toward a bottom of the cup 35.

The control of the operation of the generator using the thermocouple can follow the method disclosed in the Newmwan patents noted above. In this prior art method, the increase in the temperature of the steam generator was monitored to determine when additional water had to be injected into the steam generator. However, this method did not adequately address runaway conditions, e.g., where the rise in temperature occurred very rapidly. Thus, when controlling the generator of the invention, it is preferred to monitor the rate of change in temperature, i.e., the change in temperature over time, to determine when water should be dispensed into the steam generator. Otherwise, the control techniques of the Newman patents can be followed for operation.

Referring to FIG. 5 in connection with the inventive method, the method aspect of the invention as an improvement over the prior art techniques described in the Newman patents is now addressed. In conjunction with the inventive technique, the tubular heating coils 33 are energized to rapidly heat the thin-walled stainless steel cup 35. The rapid heat-up of the cup 35 reduces re-condensation of steam inside the generator 10. Water is then supplied via a pump or other device (not shown) to the water inlet assembly 5. Prior to water entering the bore 74 of the nozzle 13, it travels through bore 72 in the adaptor 17. Water exiting the nozzle is dispersed in a hollow conical pattern 75 and atomized into small droplets that are directed towards the previously-heated upstanding wall 71 and thermocouple end 69. Atomizing the water increases the contact surfaces between the water and the wall 71 to allow for rapid steam generation.

Once the water contacts the cup wall 71, steam is generated. This steam can then exit the steam generator via the steam outlet assembly 1, and be used for any purpose. One preferred purpose is that shown in the Newman patents, steam for sterilization of articles, such as those used in medical or dental uses. The manner in which the articles are sterilized is disclosed in the Newman patents, and a further description thereof is not necessary for understanding of the invention. However and as noted above, the rate of temperature change should be monitored for control of steam output from the steam generator rather than just the temperature increase.

Other variations in the inventive steam generator and method of use can be practiced without departing from the scope of the invention. For example, while the wall 71 is shown as upstanding, the steam generator could have other configurations in use, whereby the dispensing of the hollow cone of water may occur horizontally rather than vertically. Preferably and regardless of its orientation, the wall 71 adjacent the heating element 33 and the thermocouple end 69 should receive the hollow cone spray pattern 75 from the nozzle 13.

As noted above, the generator is made primarily of stainless steel. The cup 35, mounting stud 39, washer 63, cap 41, bracket 37, and clamp 45 are made of stainless steel, preferably an austenitic type such as 304. The fitting components for the steam outlet, water inlet and air inlet assemblies are preferably made of brass. The nozzle adapter 17 and tubes 19 are preferably made of stainless steel.

As such, an invention has been disclosed in terms of preferred embodiments thereof, which fulfills each and every one of the objects of the present invention as set forth above and provides a new and improved steam on demand generator and method of use.

Of course, various changes, modifications and alterations from the teachings of the present invention may be contemplated by those skilled in the art without departing from the intended spirit and scope thereof. It is intended that the present invention only be limited by the terms of the appended claims.

What is claimed is:

1. In a steam on demand generator comprising a cup assembly, a heating device for heating the cup assembly and an interior thereof, a water injection device for supplying water to the cup assembly, a steam outlet, and a temperature sensor positioned within the cup assembly, wherein water is supplied in quantities so that the interior of the cup assembly remains essentially dry during steam generation, the improvement comprising the cup assembly including a closed bottom thin-walled stainless steel cup formed by a stainless steel thin side wall and a bottom wall connected to the side wall and a stainless steel cap, the side wall, bottom wall, and cap forming the interior, and a hollow cone spray nozzle arranged in the stainless steel cap for supplying water onto an inside surface of the stainless steel thin side wall of the cup, wherein the heating device is brazed to an outside surface of the stainless steel thin side wall of the cup and an end portion of the temperature sensor is brazed to the inside surface of the stainless steel thin side wall of the cup.

2. The steam on demand generator of claim 1, wherein the temperature sensor is a thermocouple and at least a longitudinally-disposed side of a tip of the thermocouple directly contacts the side wall, and a tip end surface remains exposed after brazing.

3. The steam on demand generator of claim 1, wherein the heating device is a heating coil that surrounds a lower portion of the cup assembly, the lower portion including the stainless steel thin side wall.

4. In a steam on demand generator comprising a cup assembly, a heating device for heating the cup assembly and an interior thereof, a water injection device for supplying water to the cup assembly, a steam outlet, and a temperature sensor positioned within the cup assembly, wherein water is supplied in quantities so that the interior of the cup assembly remains essentially dry during steam generation, the improvement comprising the cup assembly including a closed bottom thin-walled stainless steel cup formed by a stainless steel thin side wall and a bottom wall connected to the side wall and a stainless steel cap, the side wall, bottom wall, and cap forming the interior, and a hollow cone spray nozzle in the stainless steel cap for supplying water onto an inside surface of stainless steel thin side wall of the cup, wherein the heating device is brazed to an outside surface of the stainless steel thin side wall of the cup and an end portion of the temperature sensor is brazed to the inside surface of the stainless steel thin side wall of the cup, further comprising a stainless steel stud brazed to a bottom of the stainless steel cup, the stud providing a channel for the temperature sensor to enter the interior.

5. The steam on demand generator of claim 4, wherein the temperature sensor is brazed to a portion of the stud.

6. In a steam on demand generator comprising a cup assembly, a heating device for heating the cup assembly and an interior thereof, a water injection device for supplying water to the cup assembly, a steam outlet, and a temperature sensor positioned within the cup assembly, wherein water is supplied in quantities so that the interior of the cup assembly remains essentially dry during steam generation, the improvement comprising the cup assembly including a closed bottom thin-walled stainless steel cup formed by a stainless steel thin side wall and a bottom wall connected to the side wall and a stainless steel cap, the side wall, bottom wall, and cap forming the interior, and a hollow cone spray nozzle in the stainless steel cap for supplying water to the cup, wherein the heating device and an end portion of the temperature sensor are brazed to the stainless steel cup, wherein the end portion of the temperature sensor is brazed at a location on an inside wall of the stainless steel cup, the inside wall receiving spray from the hollow cone spray nozzle, and further wherein the temperature sensor is a thermocouple and at least a side of a tip of the thermocouple directly contacts the inside wall, and a tip end surface remains exposed after brazing so that the inside wall temperature and temperature of the water inside the cup can be sensed.

* * * * *